(12) United States Patent
Lin

(10) Patent No.: US 6,394,985 B1
(45) Date of Patent: May 28, 2002

(54) BACKFLOW PROOF STRUCTURE FOR SYRINGE

(75) Inventor: Bih-Chern Lin, Taichung (TW)

(73) Assignee: Future Top Medical Environment Technic Co., Ltd., Taipei (TW)

( * ) Notice: Subject to any disclaimer, the term of this patent is extended or adjusted under 35 U.S.C. 154(b) by 0 days.

(21) Appl. No.: 09/904,907

(22) Filed: Jul. 16, 2001

(51) Int. Cl.[7] .............................................. A61M 5/315
(52) U.S. Cl. ...................................... 604/235; 604/238
(58) Field of Search ................................ 604/181, 190, 604/218, 235, 236, 238, 240

(56) References Cited

U.S. PATENT DOCUMENTS

| | | | | |
|---|---|---|---|---|
| 2,893,390 A | * | 7/1959 | Lockhart | 604/235 |
| 4,479,801 A | * | 10/1984 | Cohen | 604/238 |
| 4,952,206 A | * | 8/1990 | Ibanez et al. | 604/110 |
| 5,637,100 A | * | 6/1997 | Sudo | 604/238 |
| 5,643,224 A | * | 7/1997 | Szapiro et al. | 604/238 |
| 6,081,461 A | * | 6/2000 | Wozniak et al. | 428/66.6 |

* cited by examiner

Primary Examiner—Sharon Kennedy
(74) Attorney, Agent, or Firm—Dougherty & Troxell

(57) ABSTRACT

A backflow proof structure for a syringe comprising a central cylinder portion and two blocks positioned in a protruding end of the syringe, on the bottom of the cylinder portion is a flared portion and on the top thereof is a tip, the outer space of the tip is filled with a piece of crystallized syrup to separate a crown cap covering the top of the tip from the cylinder portion; when the cylinder portion is placed in the protruding end, and a silicone cube is placed there-beneath, an irregular-shaped stopper is placed to closely contact the bottom of the protruding end to push the crown cap on the top of the cylinder portion out of the protruding end. When the syringe and the needle are connected with each other and the cylinder portion is pressed down, the crown cap is pressed into the protruding end to form a passage; when the pressing force disappears, the silicone cube bounce the cylinder portion back to again let the flared portion block the outlet of the protruding end, this effectively prevent backflow of the injection liquid or its contact with other pollution sources.

5 Claims, 4 Drawing Sheets

BACKFLOW PROOF STRUCTURE FOR SYRINGE

BACKGROUND OF THE INVENTION

1. Field of the invention

The present invention is related to a backflow proof structure for a syringe, and especially to a backflow proof structure for a syringe which can prevent injection liquid from back flowing and from contacting with air or other pollution sources and can prevent recovery and reusing of the syringe. It can be applied for huge or small types of medical treatment establishments.

2. Description of the Prior Art

Nowadays, among huge or small medical establishments, injection is done quite frequently for medical treatments. Most syringes are made of plastic material, and it is emphasized that safe syringes will be discarded after using, and will never be used repeatedly to prevent contagion. However, if the needle had been taken away from this kind of syringe, no one can assure whether the syringe has truly been discarded or not after using, so that lack of safety becomes a major hidden crisis.

Especially for those patients who need frequent injection, such as diabetics who need insulin injection or those narcotic drug addicts who need drug injection done by themselves, the conventional syringes they use can not be effectively forced to be discarded after injection. On the contrary, continuous requiring of using syringes in a long period of time may induce the idea of repeated use of a syringe or develop a habit to use them repeatedly. By all means, under advocacy of the anti-drug spirit, actively considering protecting the drug user's sanitary behavior of injecting also has a specific value.

Moreover, after drawing out injection liquid, some syringes need to change its needle for one of a smaller size for the convenience of human body injection. But in changing the needle of a syringe, the metal needle is directly taken away from the front end of the syringe; during this short moment, the syringe without the metal needle fixed thereon might have the inside injection liquid contaminated, the injection liquid is subjected to back flowing out of the syringe. This is the second hidden crisis.

Therefore, it is the motive of the present invention to improve the above mentioned public used conventional syringes and eliminate its defects, and to provide a syringe which can prevent injection liquid from backflow and from contact with air or pollution sources and simultaneously can protect safety of patients by surely preventing recovery and reusing of the syringe.

SUMMARY OF THE INVENTION

The prime object of the present invention is to provide a structure of a syringe which can prevent backflow of injection liquid, and through the process of injection of such syringe, it can be guaranteed that there is no repeated use and can protect the body health of one who has an injection.

The secondary object of the present invention is to provide a backflow proof structure for a syringe of which the content will not contact with air or other pollution sources.

Another object of the present invention is to provide a structure which can prevent recovery and reusing of the syringe to thereby effectively guard the safety of all the national people.

To obtain the above-mentioned objects, the present invention is comprised of a central cylinder portion and a plurality of blocks which are all positioned in the protruding end of the syringe, the outer space of a tip on the top of the central cylinder portion is filled with a piece of crystallized syrup in order to separate a crown cap fitted over the top from the central cylinder portion, the central cylinder portion is placed in the protruding end, and a silicone cube is placed beneath the central cylinder portion as a pad, an irregular-shaped stopper closely contacts the bottom of the protruding end to thereby push the crown cap on top of the central cylinder portion out of the protruding end; when the syringe and the needle are connected with each other and the central cylinder portion is pressed down, the crown cap is pressed into the protruding end to form a passage; when the pressing force disappears, the silicone cube will bounce the central cylinder portion back to again let the flared portion on the bottom of the central cylinder portion block the outlet of the protruding end, this will effectively prevent backflow of the injection liquid or its contact with other pollution sources. All these are the features for the present invention.

The present invention will be apparent in its detailed structure and other features after reading the detailed description of the preferred embodiment thereof in reference to the accompanying drawings.

DETAILED DESCRIPTION OF THE PREFERRED EMBODIMENT

Figure 1:
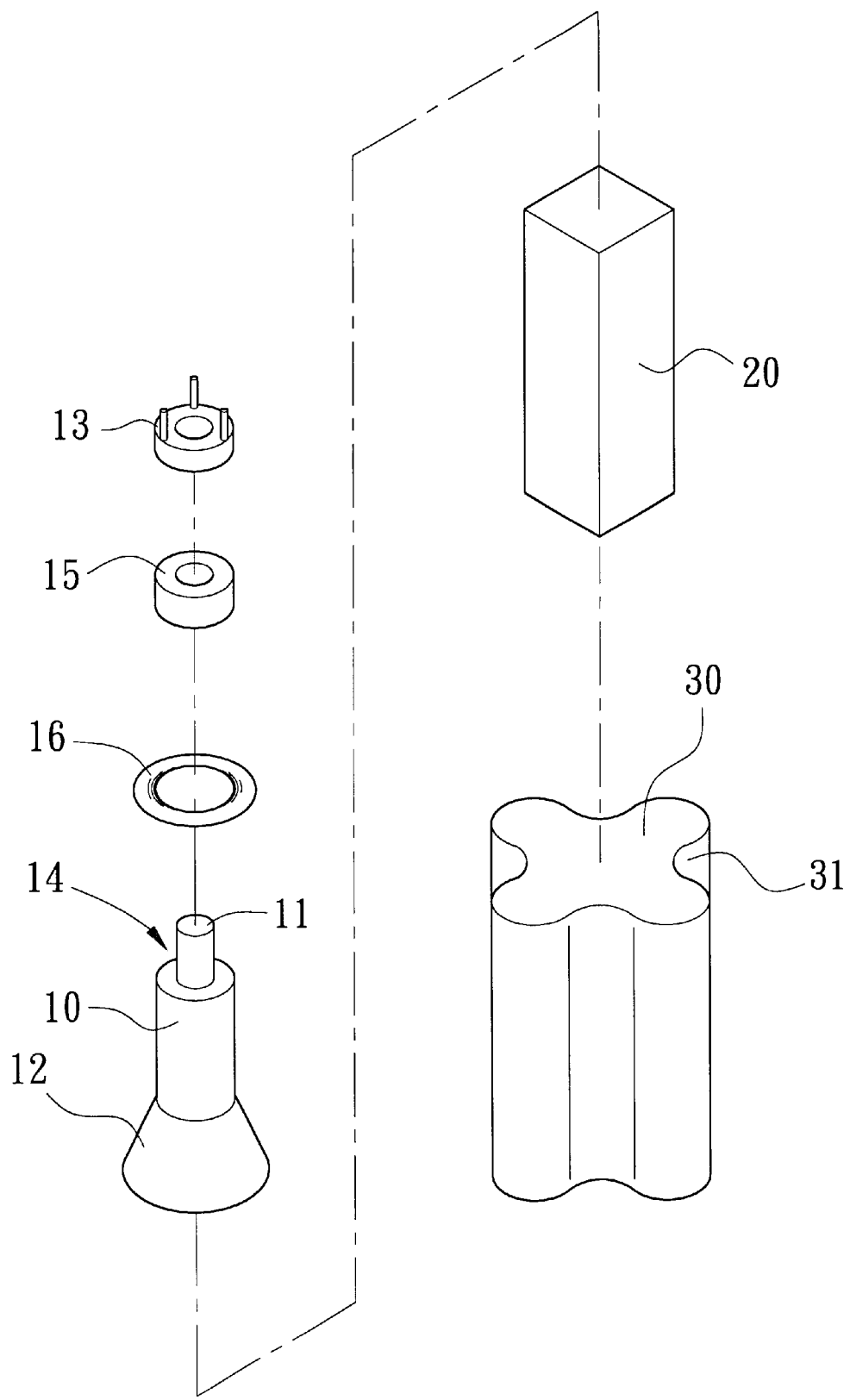
FIG. 1 is an analytic perspective view showing the elements of the embodiment of the present invention.

Referring to FIG. 1, the backflow proof structure for a syringe of the present invention mainly consists of a central cylinder portion 10, a silicone cube 20 and a stopper 30; a flared portion 12 is provided on the bottom of the central cylinder portion 10 and is fitted over with an O-shaped ring 16 at the top beginning position thereof, and a tip 11 is provided on the top of the central cylinder portion 10, the tip 11 has an outer surrounding space 14 which is filled with a piece of crystallized syrup 15 as a separating member to separate the crown cap 13 covering the top of the tip 11 from the central cylinder portion 10.

In this preferred embodiment, a plurality of blocks are placed beneath the central cylinder portion 10 and include two blocks in this embodiment, wherein the first block is the soft silicone cube 20, and the second block is the irregular-shaped stopper 30 made of hard rubber or plastic with a drilled hole in the center and surrounded with more than one longitudinal concave portions 31 for the purpose of forming gaps.

Figure 2:
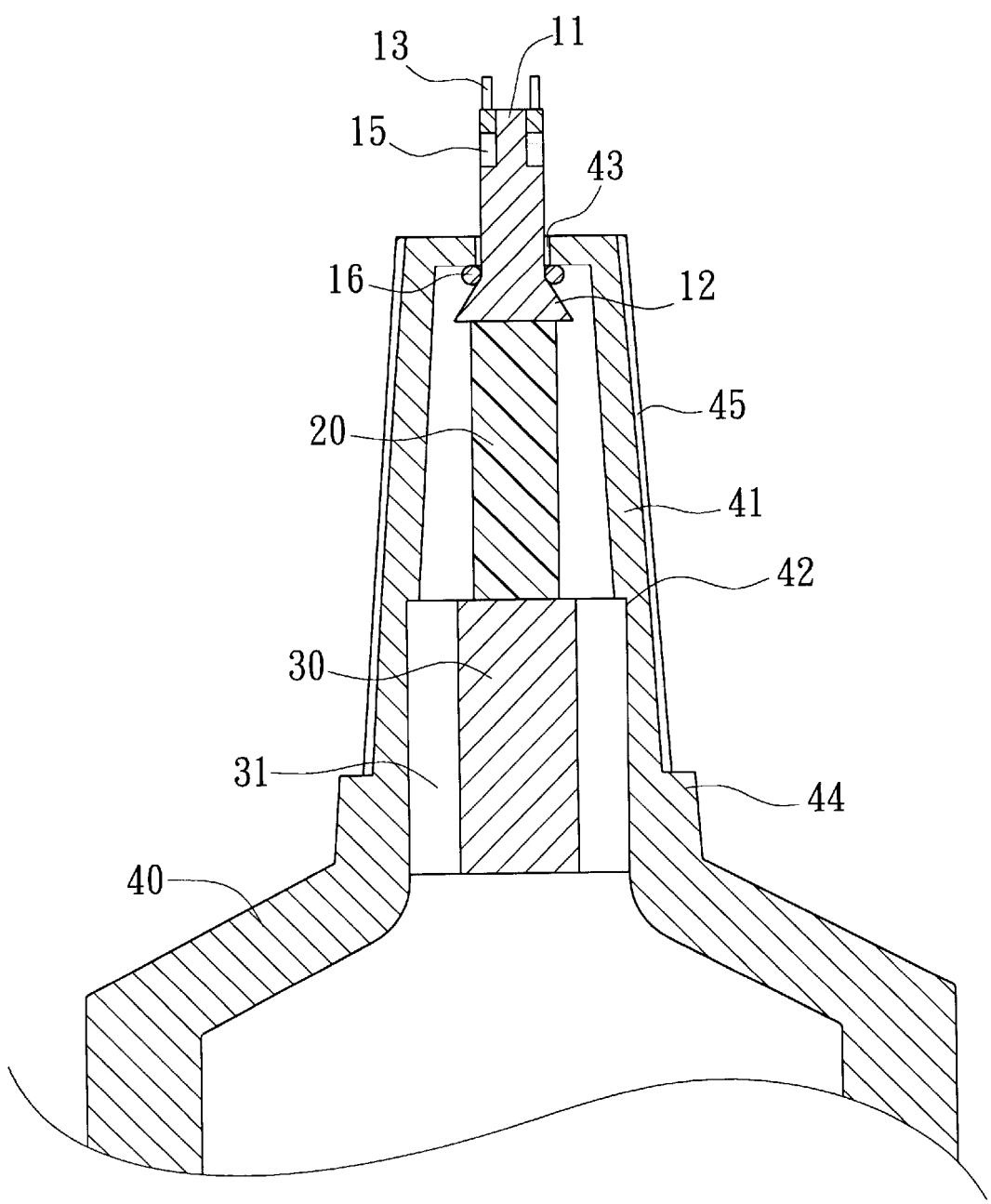
FIG. 2 is a sectional view of the assembled syringe of the embodiment of the present invention.

As shown in FIG. 2, the present invention is provided inside the protruding end 41 of the front end of the syringe 40, the inside cylindrical wall at the bottom of the protruding end 41 is a thin wall 42, and the external surface of the protruding end 41 is provided with a stepped shoulder 44. Firstly, the central cylinder portion 10 is put into the protruding end 41 to extend the crown cap 13 out of an outlet 43, then the silicone cube 20 is put on the rear part of the central cylinder portion 10, and the O-shaped ring 16 and the flared portion 12 on the bottom of the central cylinder portion 10 are abutted against the outlet 43. And then a stopper 30 is put at the rear of the silicone cube 20, since the bottom inside cylindrical wall of the protruding end 41 is the thin wall 42, it is convenient for tight fitting in and positioning of the irregular-shaped stopper 30, and the outlet 43 is sealed completely. Besides, the thin wall 42 is pressed by the stopper 30 and will possibly be deformed by pressing. In order to prevent generating a gap between the needle 50 and the protruding end 41 when they are connected with each other, the protruding end 41 is applied therearound with the crystallized syrup 45.

Figure 3:
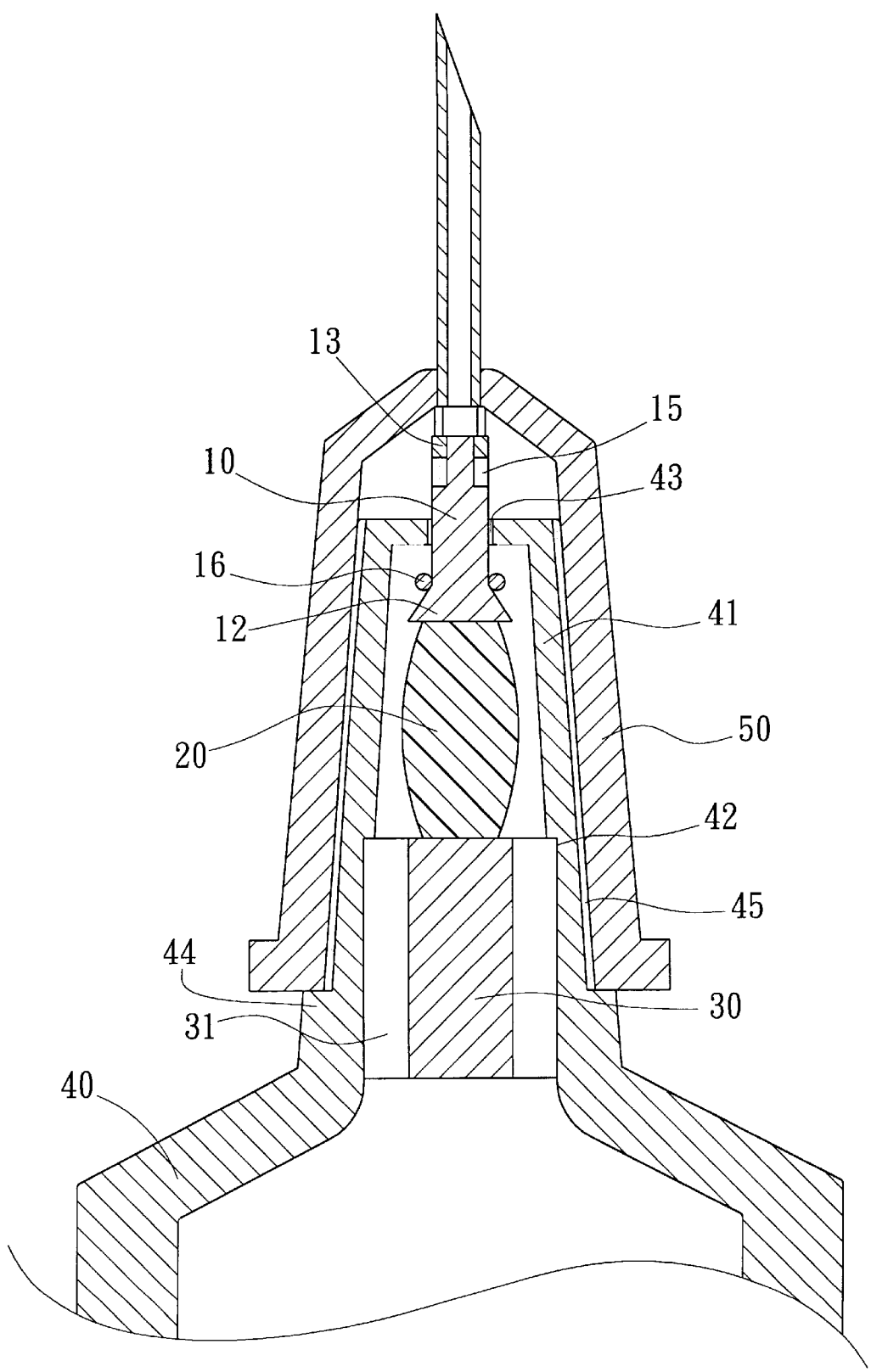
FIG. 3 is an action schematic view showing fixing of the needle of the embodiment of the present invention.
Figure 4:
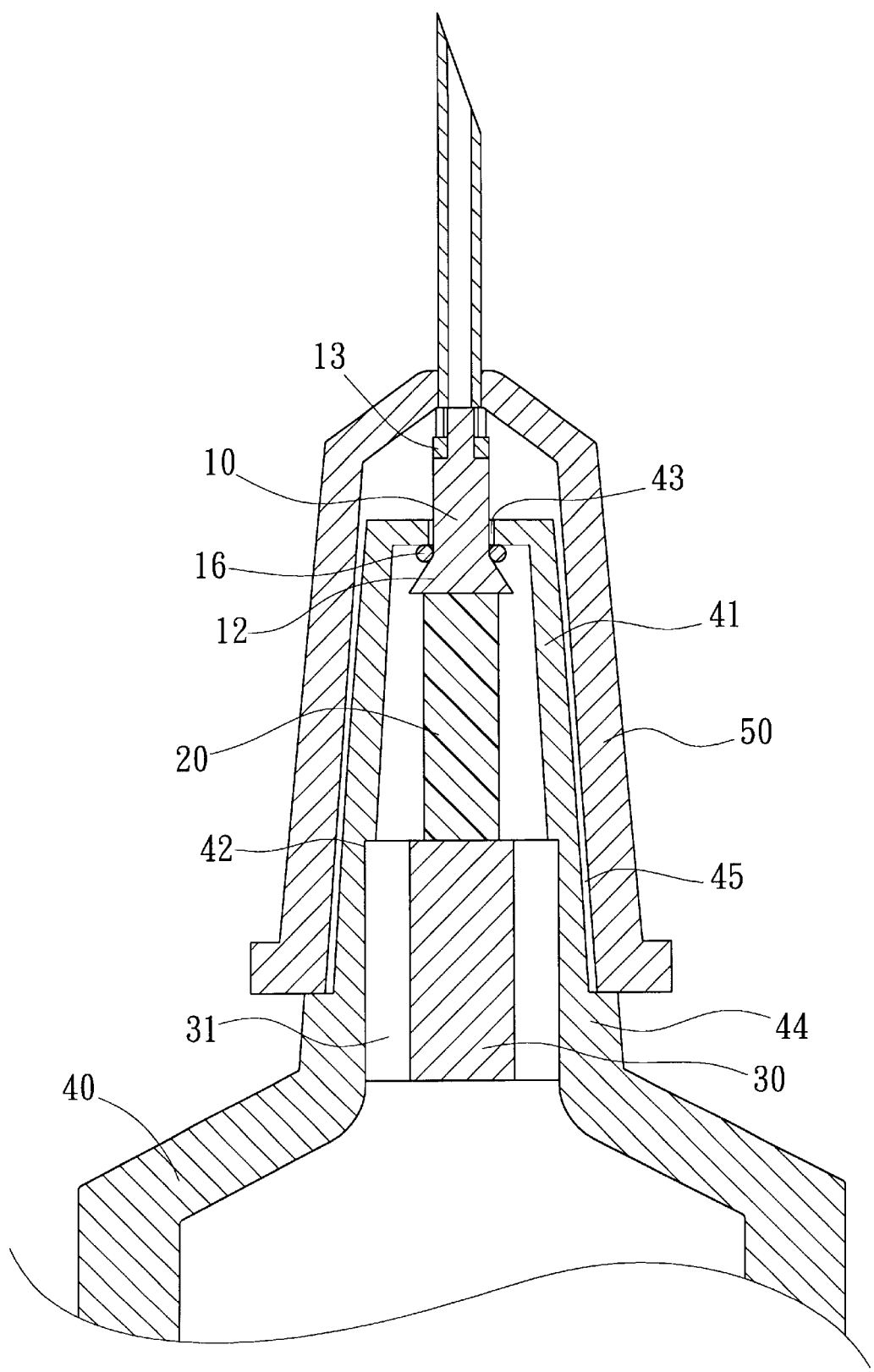
FIG. 4 is a schematic view showing completion of injection of the embodiment of the present invention.

As shown in FIGS. 3 and 4, when in completing assembling of the above-mentioned structure for the syringe 40, filling of injection liquid into the syringe 40 is also completed for use, the needle 50 is fitted over the top of the protruding end 41 and is pressed down to the stepped shoulder 44, during the process of fitting over, the crown cap 13 is under the downward pressure of the needle 50, thus the central cylinder portion 10 descends and presses the silicone 20. This will open the outlet 43 of the protruding end 41 which is covered by the flared portion 12 on the bottom of the central cylinder portion 10, and then a passage is formed between the needle 50 and the protruding end 41 (in the space beside the silicone 20 and the concave portions 31 around the stopper 30) in the syringe 40 in favor that the injection liquid inside of the syringe 40 is pushed out by a pusher rod (not shown) inside of the syringe. When the injection liquid flows out, the crystallized syrup 15 filled in the space 14 forming a separating member and the crystallized syrup 45 applied on the external surface of the protruding end 41 will be melted in contacting with injection liquid. A few minutes after completion of injection, the space 14 reappears because of the melting of the crystallized syrup 15; this makes it unable to press the silicone 20 tightly. The silicone 20 will restore to its original shape accordingly. At the same time, this will cause the flared portion 12 on the bottom of the central cylinder portion 10 to re-block the outlet 43 of the protruding end 41, and seal the outlet 43 more tightly by means of the O-shaped ring 16 to create a leakage-proof effect.

As mentioned above, melting of the crystallized syrup 15 generates a space and causes the flared portion 12 on the bottom of the central cylinder portion 10 to be unable to sink and separated from the outlet 43, then the syringe 40 can not be recovered for reusing. Moreover, if someone tries to destroy the structure of the central cylinder portion 10 and makes it possible to recover for reusing the syringe 40, since the bottom area of the protruding end 41 has the thin wall 42, once the stopper 30 is removed by excavation, the supporting force of the protruding end 41 becomes insufficient, the needle 50 can not be firmly fitted over. Meantime, the crystallized syrup 45 on the external surface of the protruding end 41 has already melted; even if the needle 50 can be fitted over the protruding end 41, upon drawing the injection liquid, it can not prevent leakage by the fact that the leakage-proof crystallized syrup 45 has fallen down. Thereby, the object of preventing recovery and reusing of the syringe 40 and effectively protecting the safety of the patients can be achieved.

In conclusion, the backflow proof structure for a syringe provided in the present invention can improve safety in using the injection syringe, and can prevent injection liquid from the chance of contacting with air or other pollution sources. There is no doubt that the structure is useful in the industry.

What is claimed is:

1. A backflow proof structure for a syringe comprising a central cylinder portion and a plurality of blocks which are positioned in a protruding end of said syringe, wherein: a flared portion is provided on the bottom of said central cylinder portion, and a tip is provided on the top of said central cylinder portion, said tip has an outer surrounding space which is filled with a piece of crystallized syrup as a separating member to separate a crown cap covering the top of said tip from said central cylinder portion; said central cylinder portion is placed in said protruding end, and a silicone cube is placed beneath said central cylinder portion, an irregular-shaped stopper is placed to closely contact the bottom of said protruding end to thereby push said crown cap on said top of said central cylinder portion out of said protruding end.

2. A backflow proof structure for a syringe as claimed in claim 1, wherein, said flared portion on said bottom of said central cylinder portion is provided on the top thereof with an O-shaped ring.

3. A backflow proof structure for a syringe as claimed in claim 1, wherein, the external surface of said irregular-shaped stopper is provided with more than one longitudinal concave portions.

4. A backflow proof structure for a syringe as claimed in claim 1, wherein, the bottom of said protruding end is provided with a thin wall for tight fitting in and positioning of said irregular-shaped stopper.

5. A backflow proof structure for a syringe as claimed in claim 1, wherein, the external surface of said protruding end of said syringe is applied with leakage-proof crystallized syrup.

* * * * *